US009538922B2

(12) United States Patent
Wang

(10) Patent No.: US 9,538,922 B2
(45) Date of Patent: Jan. 10, 2017

(54) MONITORING AN INTERVAL WITHIN THE CARDIAC CYCLE

(75) Inventor: Li Wang, Shanghai (CN)

(73) Assignee: Medtronic, Inc., Minneapolis, MN (US)

(*) Notice: Subject to any disclaimer, the term of this patent is extended or adjusted under 35 U.S.C. 154(b) by 1573 days.

(21) Appl. No.: 12/609,700

(22) Filed: Oct. 30, 2009

(65) Prior Publication Data
US 2011/0105921 A1 May 5, 2011

(51) Int. Cl.
A61B 5/02 (2006.01)
A61B 5/024 (2006.01)
A61B 5/0245 (2006.01)
A61B 5/0452 (2006.01)
A61N 1/37 (2006.01)
A61N 1/372 (2006.01)
A61B 5/00 (2006.01)
A61N 1/362 (2006.01)

(52) U.S. Cl.
CPC ............ *A61B 5/024* (2013.01); *A61B 5/0245* (2013.01); *A61B 5/0452* (2013.01); *A61N 1/3702* (2013.01); *A61N 1/37258* (2013.01); *A61B 5/7285* (2013.01); *A61N 1/3627* (2013.01)

(58) Field of Classification Search
CPC ..... A61B 5/024; A61B 5/0245; A61B 5/0452; A61B 5/7285; A61N 1/3627; A61N 1/3702; A61N 1/37258
USPC ....... 600/508, 509, 515, 518; 607/2, 3, 9, 25
See application file for complete search history.

(56) References Cited

U.S. PATENT DOCUMENTS

| 5,275,621 | A | 1/1994 | Mehra |
| 5,312,441 | A | 5/1994 | Mader et al. |
| 5,342,402 | A | 8/1994 | Olson et al. |
| 5,354,316 | A | 10/1994 | Keimel |
| 5,447,519 | A | 9/1995 | Peterson |
| 5,545,186 | A | 8/1996 | Olson et al. |
| 5,755,736 | A | 5/1998 | Gillberg et al. |
| 5,755,739 | A | 5/1998 | Sun et al. |
| 6,115,630 | A | 9/2000 | Stadler et al. |
| 6,129,744 | A | 10/2000 | Boute |
| 6,336,903 | B1* | 1/2002 | Bardy ................... 600/508 |
| 6,526,311 | B2 | 2/2003 | Begemann |
| 6,556,859 | B1 | 4/2003 | Wohlgemuth et al. |
| 6,671,549 | B2* | 12/2003 | Van Dam et al. ........... 607/25 |
| 7,027,858 | B2 | 4/2006 | Cao et al. |
| 7,139,610 | B2 | 11/2006 | Ferek-Petric |
| 7,485,095 | B2 | 2/2009 | Shusterman |

(Continued)

OTHER PUBLICATIONS

W. Zong et al., "A Robust Open-source Algorithm to Detect Onset and Duration of QRS Complexes," *Computers in Cardiology*, 2003; 30:737-740.

(Continued)

*Primary Examiner* — Christopher D Koharski
*Assistant Examiner* — Pamela M Bays
(74) *Attorney, Agent, or Firm* — Carol F. Barry

(57) ABSTRACT

Aspects of this disclosure describe measuring intervals within a cardiac cycle to, for example, determine whether a patient is a candidate for cardiac therapy initiation or modification. The intervals may be measured in response to a trigger identifying a physiological event. The intervals and an identification of the physiological event may be stored. A physician or clinician may determine whether the patient is a candidate for cardiac therapy modification based on the measured intervals.

27 Claims, 10 Drawing Sheets

(56) References Cited

U.S. PATENT DOCUMENTS

| | | |
|---|---|---|
| 7,536,224 B2 | 5/2009 | Ritscher et al. |
| 7,542,878 B2 | 6/2009 | Nanikashvili |
| 7,742,812 B2 | 6/2010 | Ghanem et al. |
| 7,761,150 B2 | 7/2010 | Ghanem et al. |
| 7,937,135 B2 | 5/2011 | Ghanem et al. |
| 8,255,047 B1 | 8/2012 | Wohlgemuth et al. |
| 8,315,709 B2 | 11/2012 | Corndorf |

OTHER PUBLICATIONS

Richard E. Klabunde, PhD, "Cardiovascular Physiology Concepts," 5 pages (Apr. 6, 2007).

* cited by examiner

MONITORING AN INTERVAL WITHIN THE CARDIAC CYCLE

TECHNICAL FIELD

The disclosure relates to implantable medical devices, and, more particularly, to collection of diagnostic information by implantable medical devices.

BACKGROUND

A variety of implantable medical devices for delivering a therapy and/or monitoring a physiological condition have been clinically implanted or proposed for clinical implantation in patients. Implantable medical devices may deliver electrical stimulation or fluid therapy to, and/or monitor conditions associated with, the heart, muscle, nerve, brain, stomach or other organs or tissue.

Some implantable medical devices, such as cardiac pacemakers or implantable cardioverter-defibrillators, provide therapeutic electrical stimulation to the heart. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Patients with heart failure are often treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle, such as the left ventricle, to synchronize its contraction with that of the right.

Some implantable medical devices, such as implantable pacemakers, or pacemaker-cardioverter-defibrillators, have been used for long term monitoring of heart failure patients. In some cases, such implantable medical devices monitor for an early indication of a heart failure decompensation event based on one or more physiological parameters of the patient. Example physiological parameters for monitoring heart failure include thoracic fluid accumulation, edema, various cardiac or vascular blood pressures, various hemodynamic parameters, nighttime heart rate, and respiration.

SUMMARY

In general, the disclosure is directed to techniques for monitoring one or more intervals within the cardiac cycle, such as the QRS width, Q-T interval, or S-T interval, via an implantable medical device (IMD). The IMD is configured to monitor one or more physiological signals, including a cardiac electrogram (EGM). In response to detecting a physiological event based on the one or more physiological signals, the IMD measures the one or more intervals, e.g., measures a QRS width.

The physiological event may be an event indicating improving or worsening cardiovascular condition, such as improving or worsening heart failure status. As examples, physiological events may include changes in heart rate variability, changes in night heart rate, or changes in thoracic fluid content, including a change that would indicate a heart failure decompensation event. As other examples, physiological events may include changes in one or more intracardiac or vascular blood pressures, changes in patient activity, changes in the frequency of sleep apnea or the occurrence of a sleep apnea, the occurrence of an atrial or ventricular tachyarrhythmia, or changes in the frequency or duration of such tachyarrhythmias.

The IMD collects the values measured for the interval or intervals in response to detecting physiological events over time. In some examples, the IMD additionally measures the one or more intervals on a periodic basis, e.g., periodically collects one measurement for the one or more intervals, or measures the intervals on a beat-to-beat basis for a period of time periodically. In some examples, the IMD additionally collects one or more measurements for the one or more intervals in response to an interrogation by a programmer or other external computing device.

A physician, clinician, caregiver, or other user may view the values of the one or more intervals measured over time via a programmer or other computing device, e.g., as a trend or in another format. The user may identify a change in the values over time, e.g., widening of the QRS complex. In some examples, the IMD, programmer, or other computing device may provide an alert based on a comparison between one or more measured intervals and one or more thresholds. The user may identify the patient as a candidate for a cardiac therapy or modification of a current cardiac therapy based on the change in the interval or alert. For example, the user may identify the patient as a candidate for CRT based on the change in the interval or alert, e.g., based on widening of the QRS complex.

In one aspect, this disclosure is directed to a method comprising identifying, with an implantable medical device (IMD) implanted within a patient, at least one physiological event, and measuring an interval within a cardiac cycle for one or more cardiac cycles in response to the identification of the at least one physiological event to generate one or more measured intervals.

In one aspect, this disclosure is directed to an implantable medical device (IMD) comprising one or more monitors configured to identify at least one physiological event of a patient, and an interval measurement unit configured to measure an interval within a cardiac cycle for one or more cardiac cycles in response to the identification of the at least one physiological event to generate one or more measured intervals.

In one aspect, this disclosure is directed to a system comprising an implantable medical device (IMD) configured to identify at least one physiological event of a patient, measure an interval within a cardiac cycle for one or more cardiac cycles in response to the identification of the at least one physiological event to generate one or more measured intervals, and transmit the one or more measured intervals, and a programmer configured to receive the one or more measured intervals and present the one or more measured intervals.

In one aspect, this disclosure is directed to a computer-readable storage medium comprising instructions that cause one or more processors in an implantable medical device (IMD) to identify at least one physiological event of a patient, and measure an interval within a cardiac cycle for one or more cardiac cycles in response to the identification of the at least one physiological event to generate one or more measured intervals.

In one aspect, this disclosure is directed to system comprising means for identifying at least one physiological event of a patient, and means for measuring an interval within a cardiac cycle for one or more cardiac cycles in response to the identification of the at least one physiological event to generate one or more measured intervals.

DETAILED DESCRIPTION

Figure 1:
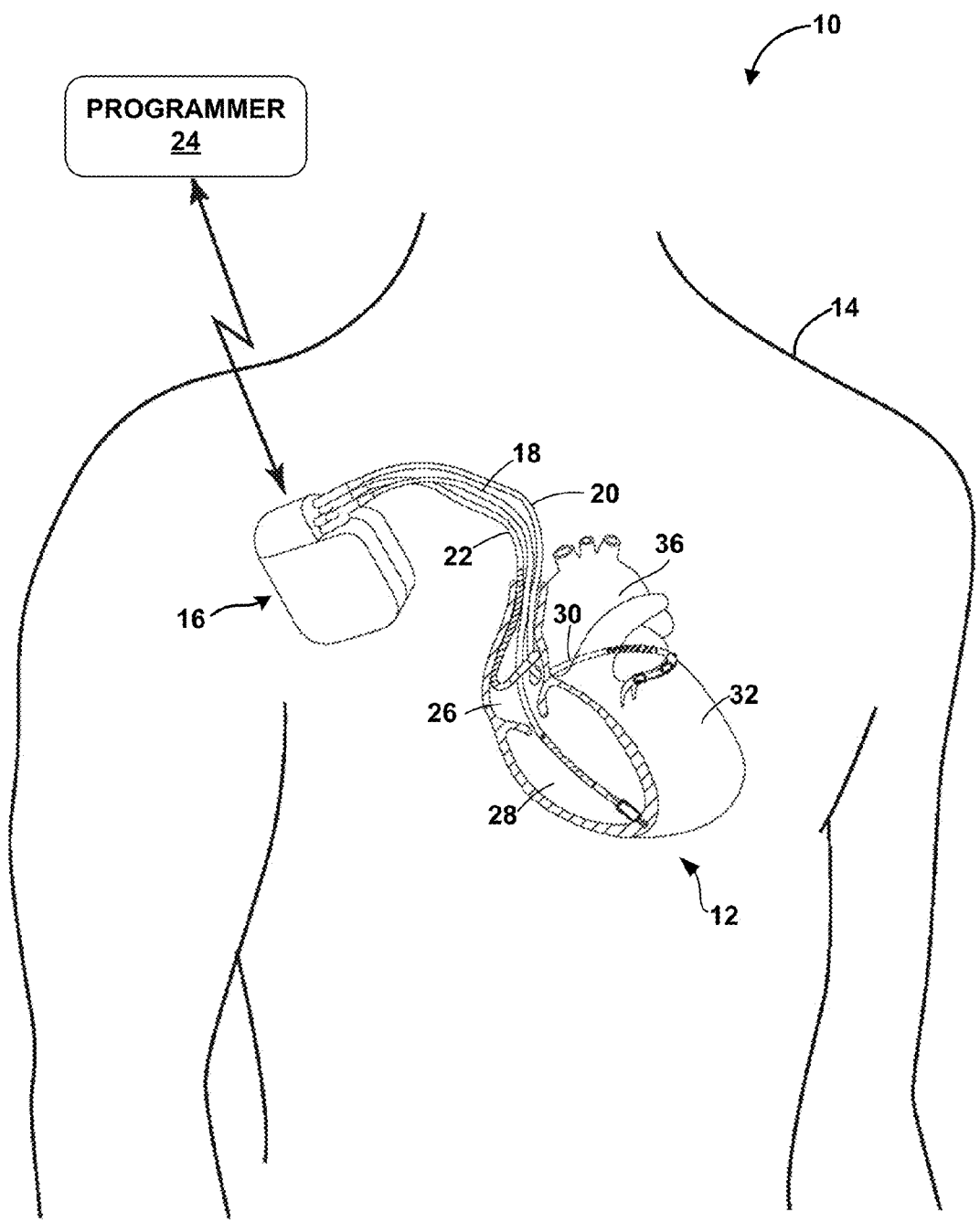
FIG. 1 is a conceptual diagram illustrating an example system comprising an implantable medical device (IMD).

FIG. 1 is a conceptual diagram illustrating an example system 10 comprising an implantable medical device (IMD) 16. System 10 may be used to monitor one or more intervals within a cardiac cycle of heart 12 of patient 14. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12. In some alternative examples, therapy system 10 may include an additional lead or lead segment (not shown in FIG. 1) that deploys one or more electrodes within the vena cava or other vein. These electrodes may allow alternative electrical sensing configurations that may provide improved sensing accuracy in some patients.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32 or premature ventricular contraction (PVC) of ventricles 28 and 32, and deliver cardioversion or defibrillation therapy to heart 12 in the form of electrical pulses. In some examples, IMD 16 may be programmed to deliver a progression of therapies, e.g., pulses with increasing energy levels, until a tachyarrhythmia of heart 12 is stopped. IMD 16 detects tachycardia or fibrillation employing one or more tachycardia or fibrillation detection techniques known in the art.

In some examples, programmer 24 may be a handheld computing device, computer workstation, or networked computing device. Programmer 24 may include a user interface that receives input from a user. It should be noted that the user may also interact with programmer 24 or IMD 16 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

As described above, IMD 16 senses the electrical signals attendant to the depolarization and repolarization of heart 12. Based on the sensed electrical activity, IMD 16 produces a cardiac electrogram (EGM) signal. As is known to those of ordinary skill in the art, the electrical activity during the cardiac cycle includes a P-wave, a QRS complex, and a T-wave for each heart beat, i.e., cardiac cycle, of heart 12. For each cardiac cycle, one or more of the P-wave, QRS complex or its components, and T-wave may be detectable by IMD 16 within the EGM.

IMD 16 is an example of a device configured to measure one or more intervals within the cardiac cycle of heart 12. As one example, an interval may be the width of the QRS complex. As other examples, an interval may be a Q-T interval or a S-T interval. In general, the techniques will be described herein with reference to the QRS width, but are equally applicable to any interval within the cardiac cycle. The interval may be measured in units of time, e.g., milliseconds (ms).

In some examples, IMD 16 may be configured to measure the interval within a cardiac cycle on a beat-to-beat basis, e.g., for a sinus rhythm. In some examples, IMD 16 may be configured to measure the interval within a cardiac cycle for one or more cardiac cycles after IMD 16 senses an event that indicates a change in a physiological condition of patient 14. In some examples, the event may be sensed by electrodes disposed on one or more of leads 18, 20, and 22, or via some other sensor. The change in a physiological condition of patient 14 triggers IMD 16 to measure the interval for one or more cardiac cycles.

Examples of physiological conditions include cardiovascular conditions such as a pressure of the heart, heart rate variability, change in impedance level related to worsening cardiovascular condition or improving cardiovascular condition, cardiac arrhythmia, and the like. Cardiac arrhythmia refers generally to any abnormal cardiac activity such as, but not limited to, premature ventricular contraction (PVC), bradycardia, ventricular tachycardia (VT), ventricular fibrillation (VF), and atrial fibrillation (AF). Examples of physiological conditions also include change in patient activity, sleep apnea, and the like. Detection of a physiological condition may be considered as a physiological event. In examples where physiological condition is a cardiovascular condition, detection of a cardiovascular condition may be considered a cardiovascular event. The physiological event may be an indication that heart 12 is progressing to a state of heart failure. The physiological event may be an indication of worsening cardiovascular condition of the patient, e.g., heart failure, or improving cardiovascular condition of the patient.

In examples where IMD 16 measures the interval for one or more cardiac cycles after detection of an event, in some examples, IMD 16 may be configured to measure the interval of a segment indicative of a cardiac cycle for one or more cardiac cycles for a certain amount of time and for a certain amount of time after the event. For example, after IMD 16 detects tachycardia or fibrillation, IMD 16 may measure the interval of a segment indicative of a cardiac cycle for one or more cardiac cycles after the tachycardia has ended. In this manner, IMD 16 may be able to provide therapy to stop the tachyarrhythmia before measuring the intervals.

In some examples, IMD 16 may be configured to measure the interval for one or more cardiac cycles upon an interrogation signal. A user of programmer 24 or another local or remote computing device may transmit the interrogation signal to IMD 16. In these examples, the interrogation signal may trigger IMD 16 to measure the interval for one or more cardiac cycles. In some examples, IMD 16 may be configured to measure the interval for one or more cardiac cycles during periodic events, e.g., every day at a certain time for a certain duration, every month at a certain day and time for a certain duration, etc.

As described above, IMD 16 may be configured to measure the QRS width for one or more cardiac cycles. For purposes of illustration, aspects of this disclosure are described with reference to the QRS width as the interval within the cardiac cycle. However, aspects of this disclosure should not be considered limited to the QRS width. Any interval within a cardiac cycle may be used in accordance with this disclosure, e.g., the QT interval, ST interval, or other intervals.

The measured intervals may allow a clinician or physician to determine whether the patient is a candidate for initiation or modification of cardiac therapy. For an individual with a healthy heart the QRS width is less than approximately 120 milliseconds (ms). For an individual progressing towards heart failure, the QRS width may be larger. If the QRS width is larger than approximately 120 ms, the patient may benefit from initiation of or modification to cardiac therapy.

For example, the clinician or physician may determine that contraction of the LV 32 and the RV 28 of heart 12 are not coordinated based on the measured QRS widths. Accordingly, the clinician or physician may recommend that patient 14 is a candidate for cardiac resynchronization therapy (CRT).

In some examples, to identify patient 14 as a candidate for cardiac therapy initiation or modification, IMD 16 may compare the QRS widths to a threshold or threshold levels at different QRS width values. The QRS widths may be measured after occurrence of an event, or may be measured continuously. If at least one of the QRS widths is greater than a threshold, IMD 16 may output an alert via programmer 24 to advise patient 14 to visit the clinician or physician. In some examples, IMD 16 may output an alert via a network (not shown in FIG. 1) to the clinician or physician indicating that patient 14 is need for cardiac therapy initiation or modification. The clinician or physician may contact patient 14 to establish a time when patient 14 should come to the clinician or physician office.

In yet some other examples, IMD 16 may be configured to provide different alerts based on the QRS width. For example, IMD 16 may be configured to provide a first alert when the QRS width is greater than a first threshold level. The first threshold level may be set to 130 ms. The first alert may comprise a recommendation that patient 14 visit the clinician or physician. The first alert may be provided via programmer 24. IMD 16 may be configured to provide a second alert when the QRS width is greater than a second threshold level, which may be set to 140 ms. The second alert may comprise a more explicit statement for patient 14 to visit the clinician or physician and may be provided to patient 14 via programmer 24 and the clinician or physician via the network. The clinician or physician may also receive the measured QRS width or widths that caused the second alert. IMD 16 may be configured to provide a third alert when the QRS width is greater than a third threshold level, which may be set to 150 ms. The third alert may comprise a very explicit statement for patient 14 to visit the emergency room and may be provided to patient 14 via programmer 24 and the clinician or physician via the network. The clinician or physician may also receive the measured QRS width or widths that caused the third alert. Upon visit to the clinician or physician or when the QRS width is send to the clinician or physician via the network, the clinician or physician may view the QRS width and determine if any initiation of cardiac therapy or modification to the current cardiac therapy is desired.

In some examples, the initiation of or modification to cardiac therapy may require modification of the system implanted within patient 14, e.g., implantation of a new IMD capable of delivering a desired therapy and/or implantation of leads needed for a desired therapy. In some examples, an IMD may be a monitor that does not provide therapy, and which may not be coupled to leads. In such examples, the physician may elect to implant a system such as that illustrated in FIG. 1 to provide CRT.

In some examples, IMD 16 may be preprogrammed with a program to provide cardiac therapy such CRT, but the program may be in a disabled state. In such examples, rather than waiting for the clinician or physician to modify cardiac therapy, IMD 16 may proactively modify the cardiac therapy based on the measured QRS widths. As before, the QRS widths may be measured after occurrence of an event, or may be measured continuously. In one example, IMD 16 may generally provide defibrillation or pacing therapy. When IMD 16 determines that the QRS width is greater than a certain threshold or threshold levels, IMD 16 may determine that patient 14 is a candidate for CRT. IMD 16 may then enable the program to provide CRT. In this manner, patient 14 may be provided with CRT without the need to visit the clinician or physician.

Aspects of this disclosure may provide various advantages. As one example, aspects of this disclosure may aid a clinician or physician to better diagnose patient 14. During a visit to the clinician or physician, subsequent to the implantation of IMD 16, patient 14 may fail to indicate the occurrence of an event of the physiological condition, and the clinician or physician may remain unaware of a more serious underlying cardiac condition. In other situations, patient 14 may indicate the occurrence of the event of the physiological condition, but the clinician or physician may fail to diagnose the more serious underlying cardiac condition. For example, patient 14 may experience sleep apnea. Patient 14 may fail to indicate that he or she is experiencing sleep apnea to the clinician or physician. In other situations, patient 14 may indicate that he or she is experience sleep apnea, and the clinician or physician may recommend treatment for the sleep apnea without recognizing a more serious underlying cardiac condition.

However, in accordance with this disclosure, IMD 16 may provide QRS width values to the clinician taken after the occurrence of the sleep apnea event. The clinician or physician may evaluate the QRS width values to determine whether the sleep apnea is related to a more serious underlying cardiac condition, such as heart 12 progressing to a state of heart failure. The clinician or physician may determine that patient 14 is a candidate for cardiac therapy initiation or modification to preemptively address the fact heart 12 may be progressing to a state of heart failure.

As another example, aspects of this disclosure may aid the physician or clinician in treating a cardiac condition determined by IMD 16. For example, IMD 16 may detect tachycardia and provide stimulation signals to treat the tachycardia. During a visit by patient 14, the clinician or physician may retrieve information indicating that patient 14 experienced tachycardia. The clinician or physician may retrieve additional information about the experienced tachycardia, and determine whether patient 14 is a candidate for cardiac therapy initiation or modification. For example, IMD 16 may be configured to measure the QRS widths after IMD 16 treated the tachycardia, i.e., after the occurrence of a physiological event which may be the tachycardia. The clinician or physician may determine whether the patient additionally experienced long QRS widths, and determine that patient 14 is a candidate for cardiac therapy initiation or modification.

As another example, aspects of this disclosure may aid the physician or clinician to preemptively address a potential deleterious cardiac condition. If the QRS widths exceed a threshold or threshold levels of QRS width values, the clinician or physician may be indicated immediately that heart 12 is progressing to cardiac failure. The clinician or physician may request that patient 14 come in for a follow up checkup to address the fact that heart 12 may be progressing to cardiac failure. Also, IMD 16 may be configured to explicit instruct patient 14 to visit the emergency room if the QRS widths exceed a threshold level. In this manner, patient 14 may be treated for a very serious cardiac condition well before patient 14 experiences the cardiac condition.

In general, the more cardiac information that is provided to the clinician or physician, the better the chances of addressing a possible cardiac condition for heart 12. Accordingly, in some examples, IMD 16 may be configured to conspicuously provide measured QRS width data that occur after the physiological condition event. Furthermore, the physician or clinician may request IMD 16 to perform QRS width measurement when patient 14 visits so that the clinician or physician has the most recent QRS width measurements for comparison with other QRS width measurements.

The configuration of system 10 illustrated in FIG. 1 is but one example. The techniques described herein may be practiced by systems that include IMDs that deliver therapies other than cardiac pacing, such as neurostimulation. Furthermore, the techniques described herein may be practiced by systems that include IMDs that do not deliver a therapy. In some examples, the techniques described herein may be practiced by a system that includes an IMD monitor, which may not be coupled to leads, and instead may sense electrical activity of heart 12 via electrodes formed on or integral with a housing of the IMD. One example of such an IMD is the Reveal® monitor, commercially available from Medtronic, Inc. In general, the techniques described herein are applicable to any IMD capable of sensing the electrical activity of the heart.

Figure 2:
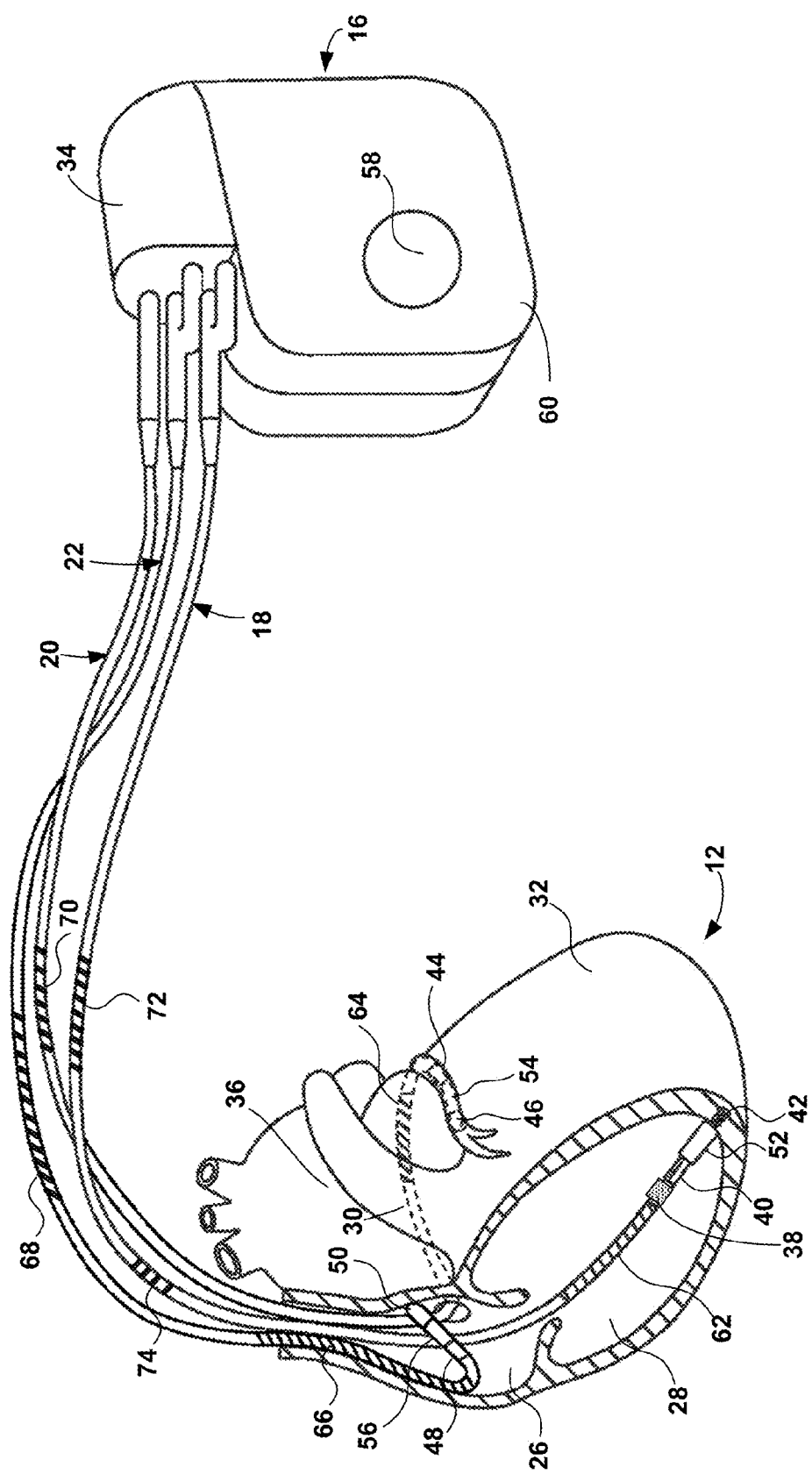
FIG. 2 is a conceptual diagram further illustrating the IMD and leads of the system of FIG. 1 in conjunction with the heart.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Pressure sensor 38 and bipolar electrodes 40 and 42 are located adjacent to a distal end of lead 18 in right ventricle 28. In FIG. 2, pressure sensor 38 is disposed in right ventricle 28. Pressure sensor 38 may respond to an absolute pressure inside right ventricle 28, and may be, for example, a capacitive or piezoelectric absolute pressure sensor. In addition, bipolar electrodes 44 and 46 are located adjacent to a distal end of lead 20 in coronary sinus 30 and bipolar electrodes 48 and 50 are located adjacent to a distal end of lead 22 in right atrium 26. There are no electrodes located in left atrium 36 in the illustrated example, but other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other embodiments, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Leads 18, 20, 22 also include elongated electrodes 68, 70, 72, respectively, which may take the form of a coil and may be external to heart 12. In FIG. 2, lead 20 may also include elongated electrode 74 which may take the form of a coil. Electrode 74 may be disposed in the superior vena cava (not shown in FIG. 2) of heart 12. Each of the electrodes 38, 40, 42, 44, 46, 48, 50, 62, 64, 66, 68, 70, 72, and 74 may be electrically coupled to a respective one of the coiled conductors within the lead body of its associated lead 18, 20, 22, and thereby coupled to respective ones of the electrical contacts on the proximal end of leads 18, 20, 22. Furthermore, the various electrodes shown in FIG. 2 are shown for illustration purposes only. Not all electrodes, e.g., electrodes 38, 40, 42, 44, 46, 48, 50, 62, 64, 66, 68, 70, 72, and 74 may be necessary in every example of system 10. For example, in some examples, IMD 16 may not be configured to measure the pressure of heart 12. In these examples, electrode 38 may not be necessary. In some examples, leads 18, 20, 22 may not comprise electrodes 68, 70, 72, respectively, or may not comprise electrodes 62, 66, 66, respectively. Aspects of this disclosure should not be considered limited to only the example electrodes shown in FIG. 2. Aspects of this disclosure may be realized by more or fewer electrodes than those referenced in this disclosure.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 5 housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12, e.g., EGM signals, via electrodes 40, 42, 44, 46, 48, 50, 58, 62, 64, 66, 68, 70, 72, and 74. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, 66, 68, 70, 72, and 74. Furthermore, any of the electrodes 40, 42, 44, 46, 48, 50, 58, 62, 64, 66, 68, 70, 72, and 74 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some embodiments may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode in the may be configured as appropriate for the application of the sensing electrode configuration.

For example, IMD 16 may sense the EGM signals between electrode 62 disposed in RV 28 and electrode 58 formed on housing 60. As another example, IMD 16 may sense the EGM signals between electrode 74 disposed in the superior vena cava and electrode 58 formed on housing 60. As yet another example, IMD 16 may sense the EGM signals between ring electrode 40 disposed in RV 28 and tip electrode 42 disposed in RV 28. As yet another example, IMD 16 may sense the EGM signals between ring electrode 40 disposed in RV 28 and electrode 58 formed on housing 60. As yet another example, IMD 16 may sense the EGM signals between at least two of electrodes 68, 70, and 72. As yet another example, IMD 16 may sense the EGM signals between one of electrodes 68, 70, and 72 and electrode 58 formed on housing 60.

In some examples, the EGM signals may be considered far-field EGM signals. The far-field EGM signals may be measured by at least two electrodes where one electrode is not disposed within a ventricle of heart 12. As a few examples, a far-field EGM signal may be measured by electrode 74 and electrode 58, electrode 66 and electrode 74, electrode 68 and electrode 72, and electrode 72 and electrode 58. The previous examples are provided for illustration purposes and should not be considered limiting.

Furthermore, as described above, IMD 16 may include one or more housing electrodes such as housing electrode 58. In examples where IMD 16 includes at least two housing electrodes (not shown in FIG. 2), IMD 16 may sense the EGM signals between at least two housing electrodes, e.g., between housing electrode 58 and another housing electrode. In examples, where IMD 16 senses the EGM signals from two housing electrodes, IMD 16 may be considered as performing leadless far-field EGM measurements.

In some examples, IMD 16 delivers pacing pulses via bipolar combinations of electrodes 40, 42, 44, 46, 48, 50, 68, 70, and 72 to produce depolarization of cardiac tissue of heart 12. In some examples, IMD 16 delivers pacing pulses via any of electrodes 40, 42, 44, 46, 48, 50, 68, 70, and 72 in combination with housing electrode 58 in a unipolar configuration. Furthermore, IMD 16 may deliver defibrillation pulses to heart 12 via any combination of elongated electrodes 62, 64, 66, 68, 70, 72, and 74 and housing electrode 58. Electrodes 58, 62, 64, 66, 68, 70, 72, and 74 may also be used to deliver cardioversion pulses to heart 12. Electrodes 62, 64, 66, 68, 70, 72, and 74 may be fabricated from any suitable electrically conductive material, such as, but not limited to, platinum, platinum alloy or other materials known to be usable in implantable defibrillation electrodes.

Similar to FIG. 1, IMD 16 of FIG. 2 may be configured to measure intervals of one or more cardiac cycles, e.g., QRS widths. The QRS width may be measured continuously or the QRS width measurement may be triggered by an occurrence of an event such as a physiological event. In some examples, IMD 16 may automatically identify the physiological event, i.e., without any user intervention, and may automatically trigger the QRS width measurement. The QRS width measurement may be used to identify whether patient 14 is a candidate for cardiac therapy initiation or modification.

Figure 3:
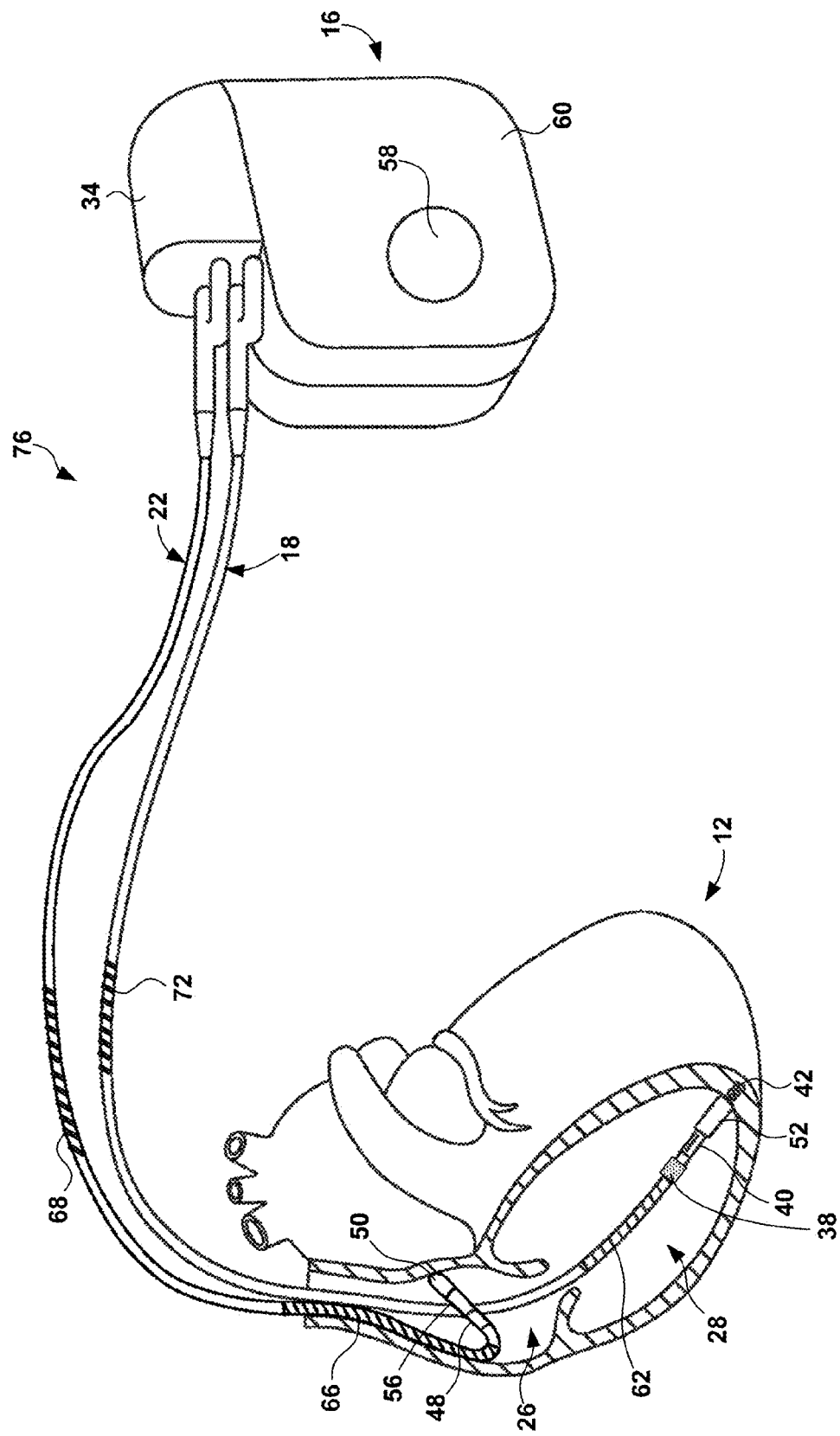
FIG. 3 is a conceptual diagram illustrating another example system comprising the IMD of FIG. 1 coupled to a different configuration of leads.

The configuration of therapy system 10 illustrated in FIGS. 1 and 2 is merely one example. In other examples, a therapy system may include epicardial or subcutaneous leads and/or patch electrodes instead of or in addition to the transvenous leads 18, 20, 22 illustrated in FIG. 1. In addition, in other examples, a system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. In other examples, as described above, an IMD need not be coupled to leads.

FIG. 3 is a conceptual diagram illustrating another example of therapy system 76, which is similar to therapy system 10 of FIGS. 1-2, but includes two leads 18, 22, rather than three leads. Leads 18, 22 are implanted within right ventricle 28 and right atrium 26, respectively. Therapy system 76 shown in FIG. 3 may be useful for providing defibrillation and pacing pulses to heart 12. Measurement of segments indicative of a cardiac cycle of heart 12 and techniques to identify whether patient 14 is a candidate for cardiac therapy medication according to the techniques described herein may also be performed by or with respect to system 76.

Figure 4:
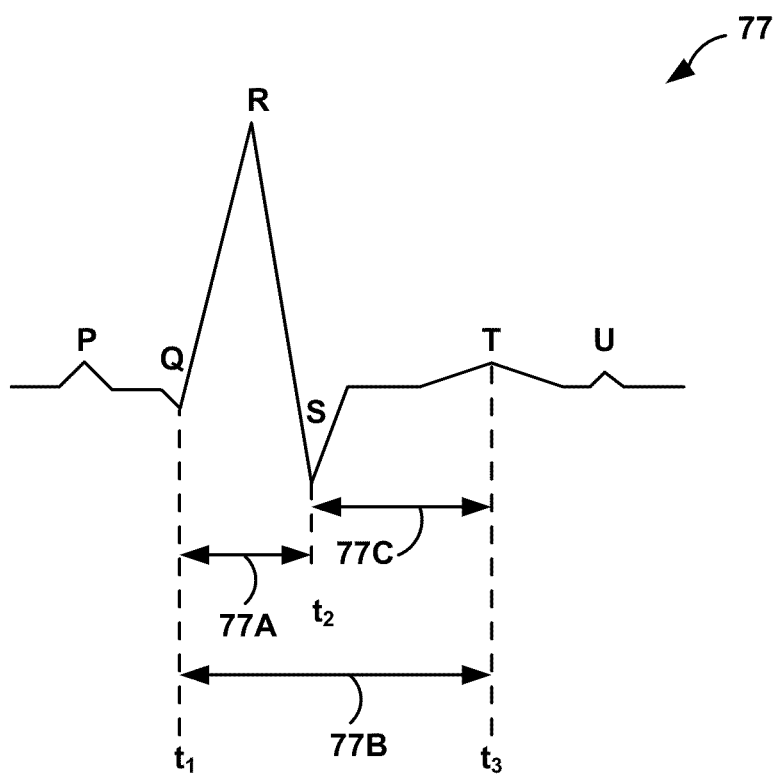
FIG. 4 is an illustration of an example of a cardiac electrogram (EGM) for a cardiac cycle.

FIG. 4 is an illustration of an example of an EGM 77 for a cardiac cycle. For purposes of illustration, EGM 77 comprises a P-wave, a Q-wave, R-wave component, S-wave, T-wave, and a U-wave, although all of these components need not identifiable in EGMs usable with the techniques described herein. Interval 77A illustrates the QRS width of EGM 77. The QRS width is the interval that includes the Q-wave, R-wave, and S-wave. Interval 77B illustrates the QT interval of EGM 77 that includes the Q-wave through the T-wave. Interval 77C illustrates the ST interval of EGM 77 that includes the S-wave and the T-wave.

Interval 77A is approximately 120 ms, i.e., $t_2-t_1$. Interval 77B is approximately 440 ms, i.e., $t_3-t_1$. Interval 77C is approximately 100 ms, i.e., $t_3-t_2$. Aspects of this disclosure are described based on measurements of the QRS width, e.g., interval 77A. However, aspects of this disclosure may by realized based on measurements of other intervals such as interval 77B, e.g., QT interval or interval 77C, e.g., ST interval.

Figure 5:
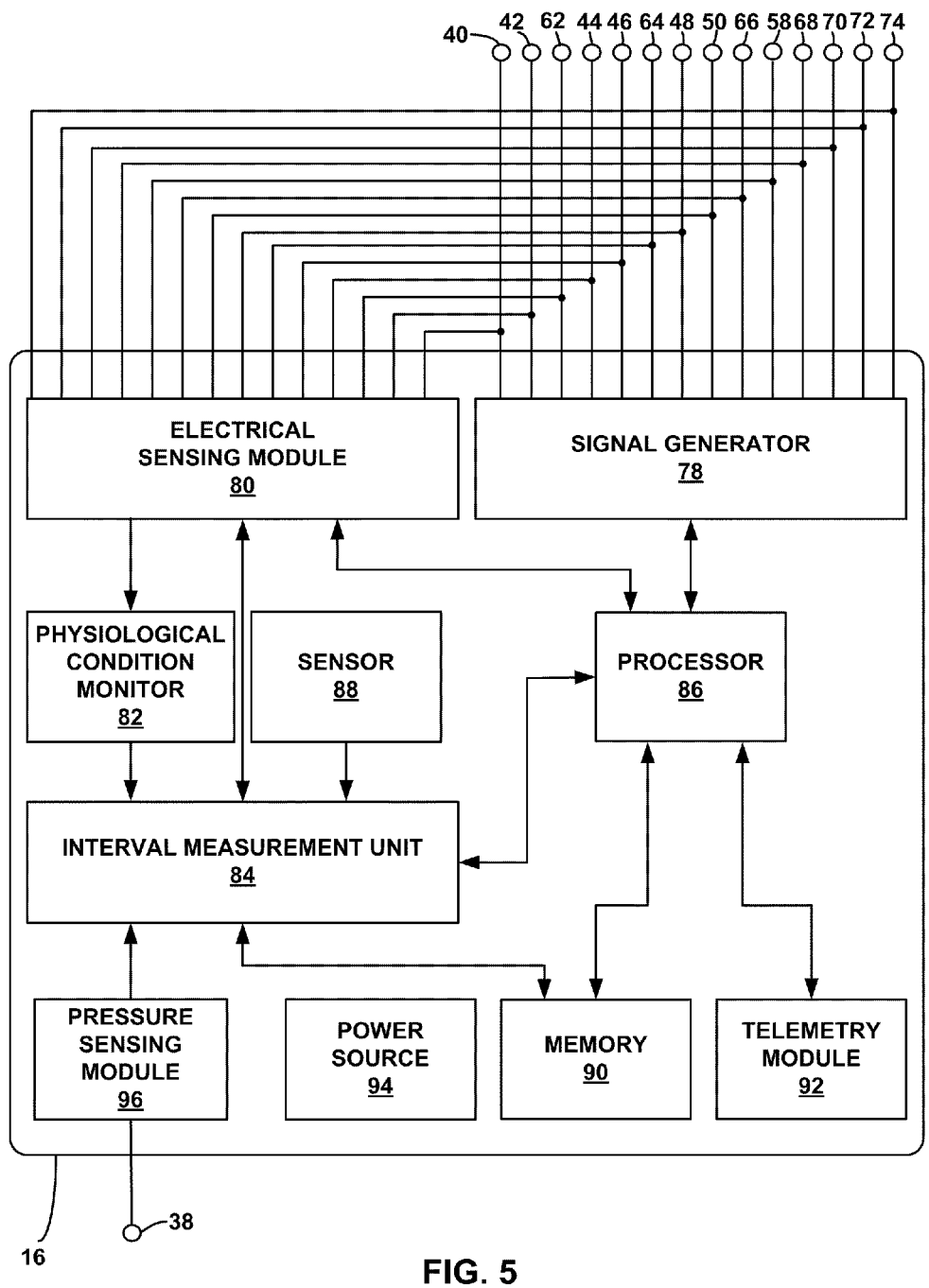
FIG. 5 is a functional block diagram illustrating an example configuration of the IMD of FIG. 1.

FIG. 5 is a functional block diagram illustrating one example configuration of IMD 16. In the example illustrated by FIG. 5, IMD 16 includes a signal generator 78, electrical sensing module 80, physiological condition monitor 82, interval measurement unit 84, processor 86, sensor 88, memory 90, telemetry module 92, power source 94, and pressure sensing module 96. Though shown as separate modules in FIG. 5, in some examples, physiological condition monitor 82 may include pressure sensing module 96 and/or sensor 88. Memory 90 may includes computer-readable instructions that, when executed by processor 86, cause IMD 16 and processor 86 to perform various functions attributed to IMD 16 and processor 86 herein. Memory 90 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 86, physiological condition monitor 82, and interval measurement unit 84 may each include any one or more of a microprocessor, a controller, a digital signal processor (DSP), an application specific integrated circuit (ASIC), a field-programmable gate array (FPGA), or equivalent discrete or integrated logic circuitry. In some examples, processor 86, physiological condition monitor 82, and interval measurement unit 84 may each include multiple components, such as any combination of one or more microprocessors, one or more controllers, one or more DSPs, one or more ASICs, or one or more FPGAs, as well as other discrete or integrated logic circuitry. The functions attributed to processor 86, physiological condition monitor 82, and interval measurement unit 84 herein may be embodied as software, firmware, hardware or any combination thereof. Furthermore, though shown as separate modules for clarity and illustration purposes, in some examples, physiological condition monitor 82 and/or interval measurement unit 84 may be formed within processor 86 such that processor 86 performs the acts attributed to physiological condition monitor 82 and/or interval measurement unit 84 that are described herein.

Processor 86 controls signal generator 78 to deliver stimulation therapy to heart 12. Processor 86 may control signal generator 78 to deliver stimulation according to a selected one or more therapy programs, which may be stored in memory 90. For example, processor 86 may control signal generator 78 to deliver electrical pulses with the amplitudes, pulse widths, frequency, or electrode polarities specified by the selected one or more therapy programs.

Signal generator 78 is electrically coupled to electrodes 40, 42, 44, 46, 48, 50, 58, 62, 64, 66, 68, 70, 72, and 74 e.g., via conductors of the respective lead 18, 20, 22, or, in the case of housing electrode 58, via an electrical conductor disposed within housing 60 of IMD 16. Signal generator 78 is configured to generate and deliver electrical stimulation therapy to heart 12. For example, signal generator 78 may deliver defibrillation shocks to heart 12 via at least two electrodes 58, 62, 64, 66, 68, 70, 72, and 74. Signal generator 78 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 78 delivers pacing, cardioversion, or defibrillation stimulation in the form of electrical pulses. In other examples, signal generator 78 may deliver one or more of these types of stimulation in the form of other signals, such as sine waves, square waves, or other substantially continuous time signals.

Signal generator 78 may include a switch module and processor 86 may use the switch module to select, e.g., via a data/address bus, which of the available electrodes are used to deliver pacing, cardioversion, or defibrillation pulses. The switch module may include a switch array, switch matrix, multiplexer, or any other type of switching device suitable to selectively couple stimulation energy to selected electrodes.

Electrical sensing module 80 monitors signals from at least one of electrodes 40, 42, 44, 46, 48, 50, 58, 62, 64, 66, 68, 70, 72, and 74 in order to monitor electrical activity of heart 12. Electrical sensing module 80 may also include a switch module to select which of the available electrodes are used to sense the heart activity. In some examples, processor 86 may select the electrodes that function as sense electrodes, or the sensing electrode configuration, via the switch module within electrical sensing module 80, e.g., by providing signals via a data/address bus. Electrical sensing module 80 may include multiple detection channels, each of which may comprise an amplifier. In response to the signals from processor 86, the switch module of within electrical sensing module 80 may couple selected electrodes to each of the detection channels.

Some detection channels may detect events, such as R- or P-waves, and provide indications of the occurrences of such events to processor 86. For example, sensing module 80 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 86 then uses that detection in measuring frequencies of the sensed events. Different narrow band channels of sensing module 80 may have distinct functions. For example, some various narrow band channels may be used to sense either atrial or ventricular events.

In some examples, sensing module 80 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 80 or processor 86. In some examples, processor 86 may store the digitized versions of signals from the wide band channel in memory 90 as electrograms (EGMs). In some examples, processor 86 may employ digital signal analysis techniques to characterize the digitized signals from the wide band channel to, for example detect and classify the patient's heart rhythm. Processor 86 may detect and classify the patient's heart rhythm by employing any of the numerous signal processing methodologies known in the art. In other examples, physiological condition monitor 82 and/or interval measurement unit 84 may analyze the EGMs, as discussed herein.

Processor 86 may maintain one or more programmable interval counters. If IMD 16 is configured to generate and deliver pacing pulses to heart 12, processor 86 may maintain programmable counters which control the basic time intervals associated with various modes of pacing, including cardiac resynchronization therapy (CRT) and anti-tachycardia pacing (ATP). In examples in which IMD 16 is configured to deliver pacing therapy, intervals defined by processor 86 may include atrial and ventricular pacing escape intervals, refractory periods during which sensed P-waves and R-waves are ineffective to restart timing of the escape intervals, and the pulse widths of the pacing pulses. As another example, processor 86 may define a blanking period, and provide signals to sensing module 80 to blank one or more channels, e.g., amplifiers, for a period during and after delivery of electrical stimulation to heart 12. The durations of these intervals may be determined by processor 88 in response to stored data in memory 90. Processor 86 may also determine the amplitude of the cardiac pacing pulses.

Processor 86 may reset interval counters upon sensing of R-waves and P-waves with detection channels of sensing module 80. For pacing, signal generator 78 may include pacer output circuits that are coupled, e.g., selectively by a switching module, to any combination of electrodes 40, 42, 44, 46, 48, 50, 58, 62, 66, 68, 70, 72, or 74 appropriate for delivery of a bipolar or unipolar pacing pulse to one of the chambers of heart 12. Processor 86 may also reset the interval counters upon the generation of pacing pulses by signal generator 78, and thereby control the basic timing of cardiac pacing functions, including CRT and ATP.

The value of the count present in the interval counters when reset by sensed R-waves and P-waves may be used by processor 86 to measure the durations of R-R intervals, P-P intervals, PR intervals and R-P intervals, which are measurements that may be stored in memory 90. Processor 86 may use the count in the interval counters to detect a tachyarrhythmia event, such as ventricular fibrillation or ventricular tachycardia. In some examples, processor 86 may identify one irregular heart beat caused by (PVC). In some examples, a portion of memory 90 may be configured as a plurality of recirculating buffers, capable of holding series of measured intervals, which may be analyzed by processor 86 to determine whether the patient's heart 12 is presently exhibiting atrial or ventricular tachyarrhythmia.

In some examples, an arrhythmia detection method may include any suitable tachyarrhythmia detection algorithms. In one example, processor 86 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 86 in other examples.

In some examples, processor 86 may determine that tachyarrhythmia has occurred by identification of shortened R-R (or P-P) interval lengths. Generally, processor 86 detects tachycardia when the interval length falls below 220 milliseconds (ms) and fibrillation when the interval length falls below 180 ms. These interval lengths are merely examples, and a user may define the interval lengths as desired, which may then be stored within memory 90. This interval length may need to be detected for a certain number of consecutive cycles, for a certain percentage of cycles within a running window, or a running average for a certain number of cardiac cycles, as examples.

Notably, the various components of IMD 16 shown in FIG. 5 and described above are provided for illustration purposes and should not be considered limiting. As described above, in some examples IMDs, in accordance with the disclosure, may be configured to sense cardiac conditions, but may not include components to provide cardiac therapy. In such examples, stimulation generator 78 may not be needed. As another example, as described above, in some examples IMDs, in accordance with the disclosure, are not coupled to leads. In such examples of IMDs, the IMDs may not be configured to provide stimulation via the leads. Accordingly, as stated above, aspects of this disclosure should not be considered limited to IMDs that provide therapy. Aspects of this disclosure may be realized by IMDs that are capable of sensing physiological events such as, but not limited to, the physiological events described herein.

An EGM may be provided to physiological condition monitor 82. Physiological condition monitor 82 may identify a physiological event. In some examples, physiological condition monitor 82 automatically identifies the physiological event. For example, physiological condition monitor 82 may be configured to identify cardiovascular conditions or events such as a, changes in heart rate variability, change in impedance level related to heart failure detection, cardiac arrhythmia, and the like. Physiological condition monitor 82 may also be configured to identify sleep apnea which may be associated with a cardiovascular condition. A more detailed example of physiological condition monitor 82 is provided in FIG. 6. Upon identification of a physiological condition event, physiological condition monitor 82 may transmit a signal to interval measurement unit 84 indicating that physiological condition monitor 82 identified a physiological condition event. The physiological condition event, and in some examples, the cardiovascular condition event, may be considered as an event indicative of heart 12 progressing to a state of heart failure or progressing away from heart failure. In general, the physiological condition event may be considered as an event indicating worsening cardiovascular condition, e.g., progressing to a state of heart failure or improving cardiovascular condition, e.g., progressing away from heart failure.

IMD 16 may comprise one or more sensors, such as sensor 88 illustrated in the example of FIG. 5. Sensor 88 may be within housing 60 (FIG. 2) of IMD 16. IMD 16 may additionally or alternatively be coupled to one or more sensors located outside of housing 60 of IMD 16. Sensor 88 may be located on or within on or more of leads 18, 20 and 22, or another lead which may or may not include stimulation/sensing electrodes. In some examples, sensor 88 may be separately housed from IMD 16, and may be coupled to IMD 16 via wireless communication. Sensor 88 may be implanted or external.

Sensor 88 may comprise, as examples, a motion sensor, a heart sound sensor, or any sensor capable of generating a signal that varies a function of mechanical activity, e.g., contraction, of heart 12. A motion sensor may be, for example, an accelerometer or piezoelectric element. In some examples, the motion sensor may indicate whether patient 14 is prone or supine, e.g., lying down. If patient 14 is prone or supine for a certain duration, patient 14 may be considered as sleeping. The motion sensor may, in some examples, indicate whether patient 14 is running, walking, or standing.

In some examples, sensor 88 may be configured to identify change in motion. For example, sensor 88 may be configured to identify when the activity level of patient 14 increases or decreases. For example, when patient 14 starts exercising, sensor 88 may identify an increase in activity level. When patient 14 stops exercising, sensor 88 may identify a decrease in activity level. Upon identifying an event indicated by the motion of patient 14, sensor 88 may transmit a signal to interval measurement unit 84 indicating that sensor 88 identified an activity or posture change event. The signal may also include an indication of when the event occurred, e.g., time and day.

IMD 16 may comprise one or more pressure sensing modules, such as pressure sensing module 96 illustrated in the example of FIG. 5. Pressure sensing module 96 may be, for example, a capacitive pressure sensor that senses an intracardiac or other cardiovascular pressure. Pressure sensing module 96 may sense cardiovascular pressure via pressure sensor 38. As described above with respect to FIG. 1, in some non-limiting examples, pressure sensor 38 may respond to an absolute pressure inside right ventricle 28, and may be, for example, a capacitive or piezoelectric absolute pressure sensor. After pressure sensing module 46 senses a pressure level greater than a threshold pressure level, or senses a change in pressure level that is greater than a threshold pressure change level, pressure sensing module 46 may transmit a signal to interval measurement unit 34 indicating an event of that the pressure level or a change in the pressure exceeding a threshold level. The signal may also include an indication of when the event occurred, e.g., time and day. The change in pressure level may be an increase or decrease in the pressure level. The pressure level or change in pressure level may be considered as an event indicative of heart 12 progressing to a state of heart failure, e.g., worsening cardiovascular condition. The pressure level or change in pressure level may be considered as an event indicative of heart 12 moving away from heart failure, e.g., improving cardiovascular condition.

Interval measurement unit 84 may be configured to measure an interval within one or more cardiac cycles based on the EGM signal sensed by electrical sensing module 80, e.g., measure the QRS width. In some examples, interval measurement unit 84 may measure the QRS width in response to an improving or worsening cardiovascular condition. For example, interval measurement unit 84 may measure the QRS width in response to an identification of PVC, AF, VF, or VT after the AF, VF, or VT has ended. In some examples, in addition to measuring the QRS width in response to and improving or worsening cardiovascular condition, interval measurement unit 84 may measure the QRS width during sinus rhythm. For example, in addition to measuring QRS widths in response to the identification of PVC, AF, VF, or VT, interval measurement unit 84 may measure the QRS width during sinus rhythm. Interval measurement unit 84 may measure the QRS width utilizing EGM signal processing techniques well known in the art.

In some examples, interval measurement unit 84 may associate an event identified by physiological condition monitor 82, sensor 88, or pressure sensing module 96 with the measured QRS width. For example, interval measurement unit 84 may associate QRS width measurements that occurred concurrently with the identification of an event. In some examples, interval measurement unit 84 may associate QRS width measurements that occurred immediately after the identification of an event for a certain duration. For example, pressure sensing module 96 may identify a change in pressure event. Interval measurement unit 84 may associate QRS widths for a duration of two minutes after the occurrence of the change in pressure event.

In some examples, instead of or in addition to measuring QRS widths for each cardiac cycle, interval measurement unit 84 may be configured to measure QRS widths in response to the occurrence of an event identified by physiological condition monitor 82, sensor 88, or pressure sensing module 96. The identification of the occurrence of an event may be done automatically. For example, physiological condition monitor 82, sensor 88, or pressure sensing module 96 may transmit a signal to interval measurement unit 84 after identification of an event. The signal may also include an indication of when the event occurred. In response to the signal from the at least one of physiological condition 82, sensor 88, or pressure sensing module 96, interval measurement unit 84 may then measure the QRS widths for cardiac cycles that occurred after the identification of the event. In other words, upon identification of an event, physiological condition monitor 82, sensor 88, or pressure sensing module 96 may trigger interval measurement unit 84 to measure the QRS widths. The measurements may be performed for a certain duration after the identification of an event, e.g., one minute. In some examples, the measurements may be performed on cardiac cycles after a certain amount of time. For example, if physiological condition monitor 82 identifies AF, VT, or VF, as some non-limiting examples, interval measurement unit 84 may measure QRS widths after the AF, VT, or VF terminated for a duration of one minute. In this manner, IMD 16 may have sufficient time to address the PVC, AF, VT, or VF.

In either example, i.e., when interval measurement unit 84 continuously measures QRS widths and associates them with identified events or when interval measurement unit 84 measures QRS widths in response to the identification of an event, interval measurement unit 84 may store an indication of the identified event, when the identified event occurred, e.g., time and day, and the measured QRS widths in memory 90. Due to the limited space available in memory 90, the measured QRS widths and the identified event may be stored in a first in first out (FIFO) fashion or a last in last out (LILO) fashion.

In some examples, to conserve space on memory 90, interval measurement unit 84 may identify QRS widths that are greater than a certain threshold, and only store QRS widths and the identified event when at least one QRS width is greater than or equal to the threshold. For example, the threshold may be 130 ms. When the QRS width is greater than or equal to 130 ms, interval measurement unit 84 may store the QRS width and the identified event associated with the QRS width or the identified event in response to which the QRS width measurements were taken, and the when the identified event occurred. In some examples where interval measurement unit 84 continuously measures the QRS widths, interval measurement unit 84 may store any measured QRS widths that that are greater than the threshold, even if there was no identified event associated with the QRS widths. Though the measured QRS widths, the identified event, and when the identified event occurred is stored in memory 90 in a FIFO or LILO fashion, QRS widths that are greater than a threshold may remain stored in memory 90 until a physician or clinician deletes the measured QRS widths and the indication of identified events in memory 90.

When patient 14 visits the clinician or physician, the clinician or physician may retrieve information stored in IMD 16 via telemetry module 92. In response to clinician or physician requesting information stored in IMD 16, processor 86 may provide the measured QRS widths, the associated identified event or the identified event in response to which interval measurement unit 84 measured the QRS widths, and when the identified event occurred. In some example, processor 86 may flag QRS widths that are greater than a threshold and the associated identified event or the identified event that triggered the QRS width measurements. The flag may conspicuously display the QRS widths that are greater than the threshold and the identified event to the physician or clinician. For example, the QRS widths that are greater than the threshold may be highlighted, presented in bold, italicized, or any combination thereof. Any technique to clearly and conspicuously display the QRS widths that are greater than the threshold and the identified event may be utilized.

In some examples, interval measurement unit 84 may be configured to provide an alert to patient 14 and/or the clinician or physician when the QRS width is greater than a threshold level. Interval measurement unit 84 may store various QRS width threshold levels. IMD 16 may be configured to provide different alerts when the QRS width exceeds the different threshold levels. For example, a first threshold level may be 130 ms. If the QRS width is greater than or equal to 130 ms, interval measurement unit 84 may transmit a signal to processor 86 indicating that the QRS width is greater than the first threshold level. In response, processor 86 may determine that a first alert to patient 14 is needed. Processor 86 may then transmit the first alert to patient 14 via telemetry module 92. Telemetry module 92 may transmit the first alert to programmer 24 or other external computing device. The first alert may comprise an instruction to patient 14 to visit the clinician or physician.

As another example, a second threshold level may be 140 ms. If the QRS width is greater than or equal to 140 ms, interval measurement unit 84 may transmit a signal to processor 86 indicating that the QRS width is greater than the second threshold level. In response, processor 86 may determine that a second alert to patient 14 and the clinician or physician is needed. Processor 86 may then transmit the second alert to programmer 24 via telemetry module 92 which may transmit the second alert to programmer 24 and the second alert to the clinician or physician via a network described in more detail with respect to FIG. 7. The second alert may comprise more explicit instructions to patient 14 to visit the clinician or physician as soon as possible.

As yet another example, a third threshold level may be 150 ms. If the QRS width is greater than or equal to 150 ms, interval measurement unit 84 may transmit a signal to processor 86 indicating that the QRS width is greater than the third threshold level. In response, processor 86 may determine that a third alert to patient 14 and the clinician or physician is needed. Processor 86 may then transmit the third alert to programmer 24 via telemetry module 92 which may transmit the third alert to programmer 24 and the third alert to the clinician or physician via a network. The third alert may comprise an even more explicit instruction to patient 14 to immediately go to the emergency room.

In some examples, some of the functionality of IMD 16 may be performed by programmer 24 or another external computing device. For example, after physiological condition monitor 82, sensor 88, or pressure sensing module 96 identify an event, IMD 16 may transmit the indication of the identified event to programmer 24. Programmer 24 may then transmit a signal to IMD 16 indicating that interval measurement unit 84 should measure the QRS widths. The measured QRS widths may be transmitted back to programmer 24 for storage. Based on the measured QRS widths, programmer 24 may identify whether an alert is needed. Programmer 24 may then transmit the appropriate alert, e.g., whether patient 14 should visit the physician or clinician, whether patient 14 should visit the physician or clinician as soon as possible, or whether patient 14 should immediately visit the emergency room. In other examples, programmer 24 or another external computing device may include a physiological condition monitor 82, pressure sensing module 96, and/or interval measurement unit 84. The programmer or other device may receive EGM and other physiological parameter signals from IMD 16, and may process the signals to identify physiological events and measure intervals within cardiac cycles, as described herein with respect to IMD 16.

Based on the measured QRS widths, the physician and clinician may be better suited to diagnose patient 14. For example, the physician or clinician may recognize that the QRS widths increased relative to an ideal QRS width in conjunction with the occurrence of a particular event, e.g., sleep apnea. The physician or clinician may recognize that one possible reason why patient 14 is experiencing sleep apnea is because heart 12 is progressing to a state of heart failure. Accordingly, the physician or clinician may recommend patient 14 as a candidate for cardiac therapy initiation or modification. By initiating cardiac therapy or modifying the cardiac therapy to address the possible heart failure, patient 14 may no longer experience sleep apnea. As another example, patient 14 may experience VT. To treat the VT, patient 14 may ingest medication. Upon a visit to the physician or clinician, the physician or clinician may recognize that the QRS width after VT increased greatly and returned to normal intervals after a relatively long duration. Accordingly, the physician or clinician may recognize that the current cardiac therapy, e.g., ingestion of medication, is insufficient to address future deleterious cardiac conditions. The physician or clinician may then recommend cardiac therapy modification to preemptively address possible future deleterious cardiac conditions. Simply put, by recognizing which events caused the increase in QRS widths, the physician or clinician can recognize how to better treat patient 14.

In addition to automatic triggering of interval measurements, patient 14, the physician, or the clinician may proactively trigger interval measurement unit 84 to measure QRS widths. For example, patient 14, the physician, or the clinician, via programmer 24, may transmit a signal to IMD 16 to trigger interval measurement unit 84 to measure QRS widths. Telemetry module 92 may receive the signal and transmit the signal to processor 86. In response, processor 86 may trigger interval measurement unit 84 to measure the QRS widths. In response, interval measurement unit 84 may then measure the QRS widths and provide the QRS width measurements to processor 86. Processor 86 may then provide the measured QRS widths to telemetry module 92 for transmission to programmer 24.

Telemetry module 92 includes any suitable hardware, firmware, software or any combination thereof for communicating with another device, such as programmer 24 (FIG. 1). Under the control of processor 86, telemetry module 92 may receive downlink telemetry from and send uplink telemetry to programmer 24 with the aid of an antenna, which may be internal and/or external. Processor 86 may provide the data to be uplinked to programmer 24 and the control signals for the telemetry circuit within telemetry module 92, e.g., via an address/data bus.

The various components of IMD 16 are coupled to power source 98, which may include a rechargeable or non-rechargeable battery. A non-rechargeable battery may be capable of holding a charge for several years, while a rechargeable battery may be inductively charged from an external device, e.g., on a daily or weekly basis.

Figure 6:
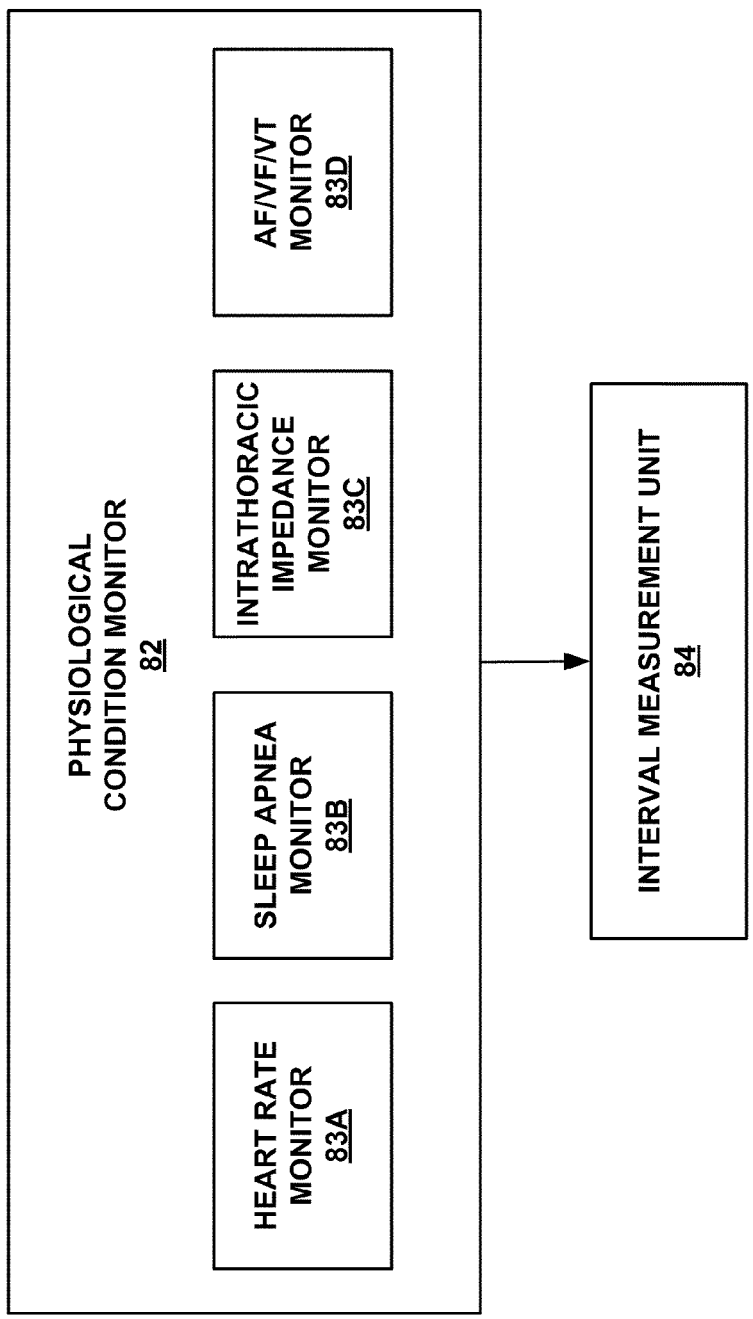
FIG. 6 is a functional block diagram illustrating one example configuration of a physiological condition monitor in greater detail.

FIG. 6 is a functional block diagram illustrating one example configuration of physiological condition monitor 82 in greater detail. For purposes of clarity, various other modules of IMD 16 are not shown in FIG. 6. Physiological condition monitor 82 comprises heart rate monitor 83A, sleep apnea monitor 83B, intrathoracic impedance monitor 83C, and AF/VF/VT monitor 83D (collectively referred to as monitors 83). Monitors 83 are shown for purposes of illustration. Aspects of this disclosure should not be considered limited to only monitors 83. Physiological condition monitor 82 may comprise more or fewer monitors than monitors 83. Any monitor that monitors any physiological parameter of a patient may be utilized in accordance with this disclosure. For example, physiological condition monitor 82 may include a monitor for identifying any occurrence of PVC. In some examples, monitors 83 may be identify an event indicative of heart 12 progressing to or moving away from a state of heart failure.

Heart rate monitor 83A may be configured to measure the heart rate of heart 12. The heart rate refers to the number of cardiac cycles for a given unit of time, e.g., beats per minutes. Heart rate monitor 83A may measure the heart rate of heart 12 via one or more electrodes disposed on leads 18, 20, and 22. In some examples, heart rate monitor 83A may measure the heart rate of heart 12 via an electrode disposed on any one of leads 18, 20, and 22 and electrode 58. In some examples, heart rate monitor 83A may measure the heart rate via acoustic sensors or piezoelectric sensors. In general, heart rate monitor 83A may utilize any techniques known in the art to measure the heart rate of heart 12.

In some examples, if the heart rate increases beyond a threshold or decreases beyond a threshold, heart rate monitor 83A may output a signal of a physiological event, and more particular, a cardiovascular event, indicating that heart 12 has sped up beyond the threshold or slowed down beyond the threshold. Heart rate monitor 83A may transmit the indication of the cardiovascular event to interval measurement unit 84.

In some examples, heart rate monitor 83A may be configured to detect a change in the heart rate. For example, it may be possible for the heart rate to suddenly increase or decrease but still be below or above the thresholds. Heart rate monitor 83A may measure the amount the heart rate changed. If the change in heart rate is greater than a threshold, heart rate monitor 83A may transmit the indication of a cardiovascular event to interval measurement unit 84.

In some examples, heart rate monitor 83A and sensor 88 may work in concert to identify a cardiovascular event. For example, heart rate monitor 83A may be configured to measure the heart rate only when patient 14 is sleeping. When sensor 88 identifies that patient 14 is in a prone or supine position for a certain duration, e.g., 30 minutes, patient 14 may be sleeping. Upon an indication that patient 14 is sleeping, heart rate monitor 83A may begin measuring the heart rate, e.g., night or sleep heart rate, of patient 14. In some additional examples, heart rate monitor 83A may be configured to measure the heart rate for a certain time when it is most likely that patient 14 is sleeping, e.g., start at 10 pm and stop at 8 am. As before, based on an identified cardiovascular event, e.g., when heart rate is higher or lower or when the change in heart rate is relatively high or low, heart rate monitor 83A may transmit the indication of the physiological, e.g., cardiovascular, event to interval measurement unit 84. In general, increasing night heart rate may be a sign of worsening cardiovascular condition, e.g., progression of heart failure, and decreasing night heart rate may be a sign of improving cardiovascular condition, e.g., moving away from heart failure, Sleep apnea monitor 83B may be configured to detect sleep apnea in patient 14. When patient 14 experiences sleep apnea, patient 14 stops breathing during sleep which causes patient 14 to wake up. Accordingly, techniques used to detect respiration may be used to detect sleep apnea. Sleep apnea monitor 83B may work in concert with sensor 88. Sensor 88 may first determine whether patient 14 is asleep as described above. Sleep apnea may then determine whether patient 14 stopped breathing while asleep.

Sleep apnea monitor 83B may utilize any techniques known in the art to detect respiration. For example, respiration may be represented as noise on the EGM signal generated by electrical sensing module 80 via one or more electrodes disposed on leads 18, 20, or 22 or via one electrode lead 18, 20, or 22 and electrode 58. Sleep apnea monitor 83B may filter the EGM signal to detect the noise level. If the noise level is below a threshold, sleep apnea monitor 83B may determine that patient 14 is experiencing a sleep apnea event.

As another example, sleep apnea monitor 83B may include piezoelectric sensors or acoustic sensors that measure the movement of the diaphragm or thorax. If the movement of the diaphragm or thorax stops, sleep apnea monitor 83B may determine that patient 14 is experiencing a sleep apnea event. As yet another example, sleep apnea monitor 83B may work in concert with intrathoracic impedance monitor 83C to measure the intrathoracic impedance of patient 12. Based on the intrathoracic impedance, sleep apnea monitor 83B may identify respiration, and identify a sleep apnea event. When sleep apnea monitor 83B identifies a sleep apnea event, sleep apnea monitor 83B may transmit the indication of the sleep apnea event to interval measurement unit 84. The sleep apnea event is an example of the physiological condition event.

Intrathoracic impedance monitor 83C may be configured to measure the intrathoracic impedance. Fluid accumulation in the thoracic cavity may be an indication that heart 12 is progressing to heart failure. Intrathoracic impedance monitor 83C may be configured to detect the fluid build up based on the intrathoracic impedance. If the intrathoracic impedance is greater than a threshold value, intrathoracic impedance monitor 83C may transmit the indication of a physiological event to interval measurement unit.

AF/VF/VT monitor 83D may be configured to identify AF, VF, or VT in patient 14. Any technique known in the art may be used to identify AF, VF, or VT. For example, the techniques described above with respect to FIG. 5 may be used to identify AF, VF, or VT. In some examples, monitor 83D may be configured to identify PVC. Upon detection of AF, VF, or VT, AF/VF/VT monitor 83D may transmit the indication of the cardiovascular event to interval measurement unit 84. In some examples, upon detection of PVC, monitor 83D may transmit the indication of the cardiovascular event to interval measurement unit 84.

As described above, in some examples, interval measurement unit 84 may continuously measure the QRS widths. Upon identification of one or more events via monitors 83, interval measurement unit 84 may associate the identified event with the QRS width measurements and store the identified event, the associated QRS width measurements, and when the identified event occurred. In some examples, one or more events identified by monitors 83 may trigger interval measurement unit 84 to measure the QRS widths. In some examples, interval measurement unit 84 may measure the QRS widths for a certain duration after the identification of the event. For example, in response to an identification of an event, interval measurement unit 84 may measure the QRS widths for each cardiac cycle for a duration of two minutes. In some examples, in response to an identification of an event, interval measurement unit 84 may wait for a certain duration before measuring the QRS widths. For example, after a cardiovascular event, interval measurement unit 84 may wait one minute to measure the QRS widths and may then measure the QRS widths for a duration of two minutes. In some examples, when AF/VF/VT monitor 83D identifies an AF, VF, or VT event, interval measurement unit 84 may measure the QRS widths after the termination of the AF, VF, or VT event. AF, VF, or VT may be a sign of heart 12 progressing to a state of heart failure. Measuring the QRS widths after the termination of the AF, VF, or VT, i.e., during sinus rhythm, may provide the clinician or physician with information regarding the condition of heart 12.

Figure 7:
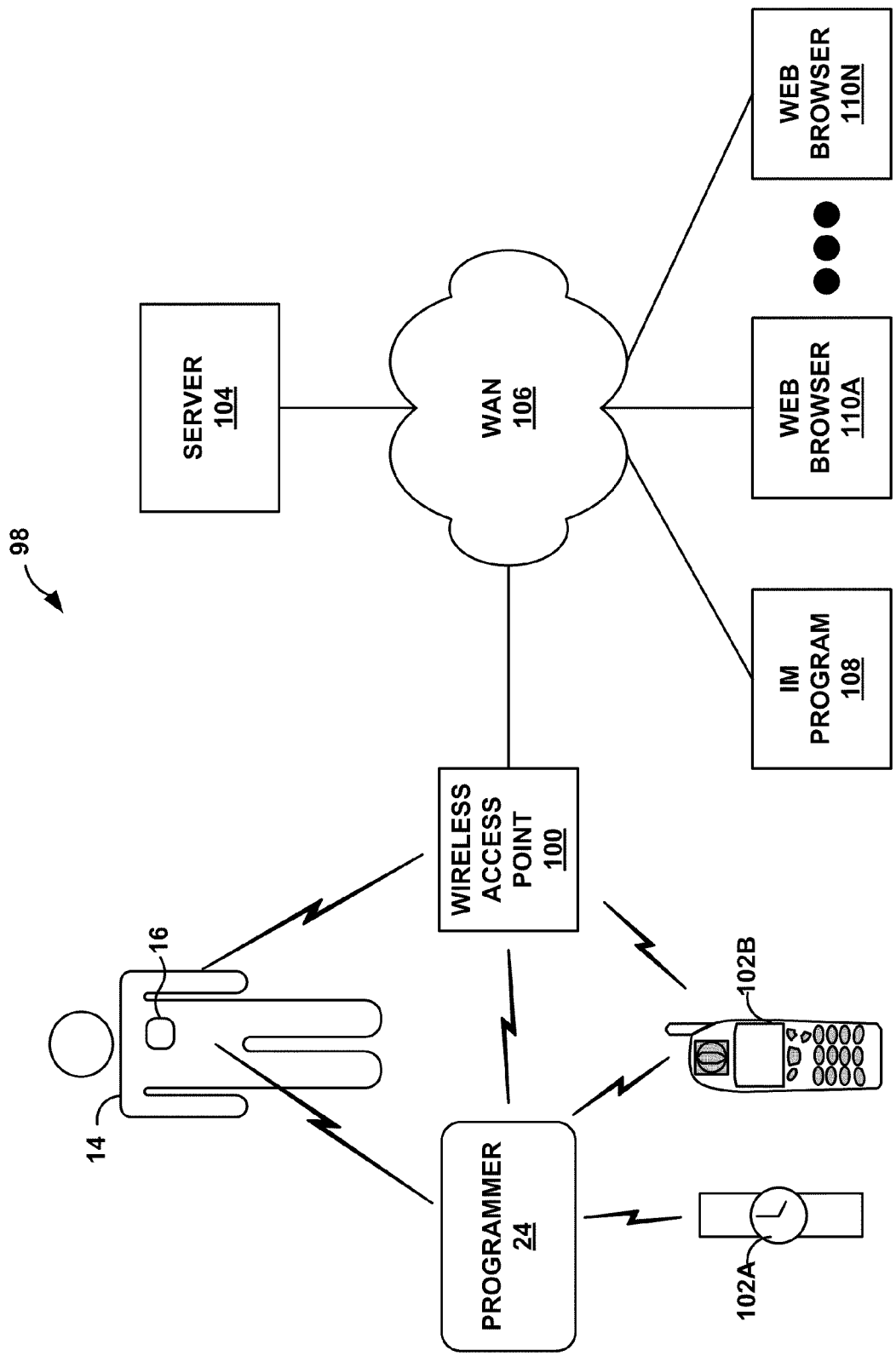
FIG. 7 is a block diagram illustrating an example system in which an IMD implanted within patient transmits measured QRS widths to devices external to the patient.

FIG. 7 is a block diagram illustrating an example system 98 in which an IMD 16 implanted within patient 14 transmits measured QRS widths to devices external to patient 14. System 98 includes patient 14 implanted with IMD 16. As shown in FIG. 7, IMD 16 communicates wirelessly with programmer 24 via radio frequency (RF) telemetry, but the communication may also be transmitted via a wired connection, an optical connection, or a transcutaneous communication link. As noted above, programmer 24 may be a patient programmer, i.e., a device dedicated to receiving user input pertaining to electric stimulation and transmitting corresponding commands to IMD 16. IMD 16 may be interrogated by, or may voluntarily transmit information to, programmer 24. As discussed above, the information obtained from IMD 16 may include measured QRS widths, identified events associated with the measured QRS widths or identified events that triggered the measurement of QRS widths, and when the identified events occurred. Also, as discussed above, IMD 16 may transmit information indicating the QRS widths, the identified events, and when the identified events occurred automatically when the QRS widths are greater than a threshold level.

As shown, programmer 24 may communicate with general purpose devices 102A, 102B. In the illustrated example, programmer 24 communicates with general purpose devices including a wristwatch 102A and a cellular telephone 102B. In other examples, programmer 24 may communicate with a pager, personal digital assistant (PDA), or other general purpose device (not shown), which may be carried by patient 14. General purpose devices 102 may display text or graphical indications to patient 14. In some examples, programmer 24 may itself be a general purpose device such as a pager, cellular telephone, or PDA.

Programmer 24 may transfer information to a docking station (not shown) upon being placed in the docking station. In other embodiments, programmer 24 may wirelessly transfer data to wireless access point (WAP) 100. Alternatively, IMD 16 may communicate directly with WAP 100. WAP 100 may communicate information to cellular telephone 102B. In some embodiments, WAP 100 may transfer information to a server 104 via wide area network (WAN) 106. Server 104 may be a central server of a patient management system located at the clinician or physician office, and WAN 106 may be the Internet. In this manner, IMD 16 may transmit QRS widths, identified events, and when the identified events occurred to the physician or clinician.

Server 104 may present web pages containing information via web browsers 110A-110N (collectively referred to as web browsers 110) to users such as patient 14, or a physician or clinician of patient 14. Server 104 may also present information via an instant message (IM) program 108 to patient 14 or other users. Patient 14 may view the information presented by web browser 110A and IM program 108 on a home computer. For example, server 104 may cause patient 14 to receive an alert via wristwatch 102A, cellular telephone 102B, or IM program 108 that instructs patient 14 to visit the clinician or physician because the QRS width has increased beyond a threshold level.

Information such as the QRS widths, identified events, and when the identified events occurred may be presented to patient 14 and/or other users (e.g., a physician or clinician) by any of programmer 24, devices 102, web browsers 110 or IM program 108. Information may be presented via visible or audible output media provided by programmer 24, such as lights, LEDs, a display or an audio speaker. An audio message may take the form of an audible beep, ring, speech message or the like. In some examples, the information provided to patient 14 or the physician or clinician may be presented in a very clear and conspicuous manner. In particular, information related to occurrences of the QRS width being relatively larger than normal QRS widths may be presented in a very clear and conspicuous manner.

The system of FIG. 7 may be implemented, in some aspects, with general network technology and functionality similar to that provided by the Medtronic CareLink® Network developed by Medtronic, Inc., of Minneapolis, Minn.

Figure 8:
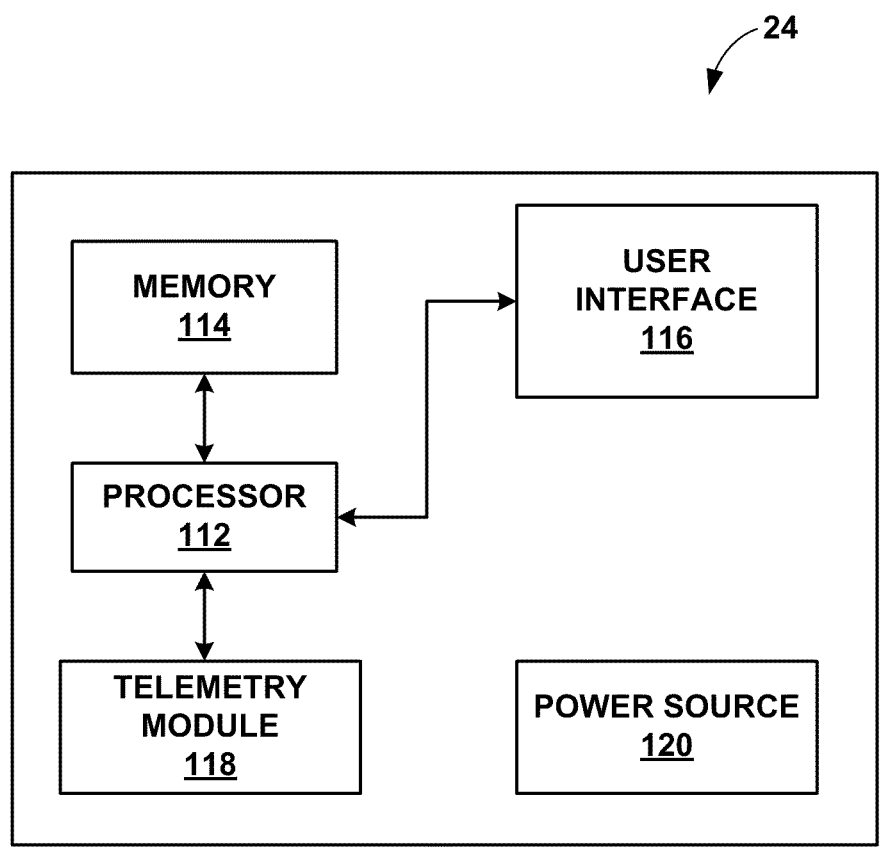
FIG. 8 is a functional block diagram of an example configuration of the external programmer shown in FIG. 1, which facilitates user communication with an IMD.

FIG. 8 is block diagram of an example programmer 24. As shown in FIG. 8, programmer 24 includes processor 112, memory 114, user interface 116, telemetry module 118, and power source 120. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 116 which may include display to present graphical user interface to a user, and a keypad or another mechanism for receiving input from a user.

Processor 112 can take the form one or more microprocessors, DSPs, ASICs, FPGAs, programmable logic circuitry, or the like, and the functions attributed to processor 112 herein may be embodied as hardware, firmware, software or any combination thereof. Processor 112 of programmer 24 may provide any of the functionality ascribed herein to processor 86 of IMD 16, or otherwise perform any of the methods described herein.

Memory 114 may store instructions that cause processor 112 to provide the functionality ascribed to programmer 24 herein, and information used by processor 112 to provide the functionality ascribed to programmer 24 herein. Memory 114 may include any fixed or removable magnetic, optical, or electrical media, such as RAM, ROM, CD-ROM, hard or floppy magnetic disks, EEPROM, or the like. Memory 114 may also include a removable memory portion that may be used to provide memory updates or increases in memory capacities. A removable memory may also allow patient data to be easily transferred to another computing device, or to be removed before programmer 24 is used to program therapy for another patient. Memory 114 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 118, which may be coupled to an internal antenna or an external antenna. An external antenna that is coupled to programmer 24 may correspond to the programming head that may be placed over heart 12, as described above with reference to FIG. 1. Telemetry module 118 may be similar to telemetry module 92 of IMD 16 (FIG. 5).

Telemetry module 118 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Power source 120 delivers operating power to the components of programmer 24. Power source 120 may include a battery and a power generation circuit to produce the operating power. In some embodiments, the battery may be rechargeable to allow extended operation. Recharging may be accomplished by electrically coupling power source 120 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 120 may include circuitry to monitor power remaining within a battery. In this manner, user interface 116 may provide a current battery level indicator or low battery level indicator when the battery needs to be replaced or recharged. In some cases, power source 120 may be capable of estimating the remaining time of operation using the current battery.

Figure 9:
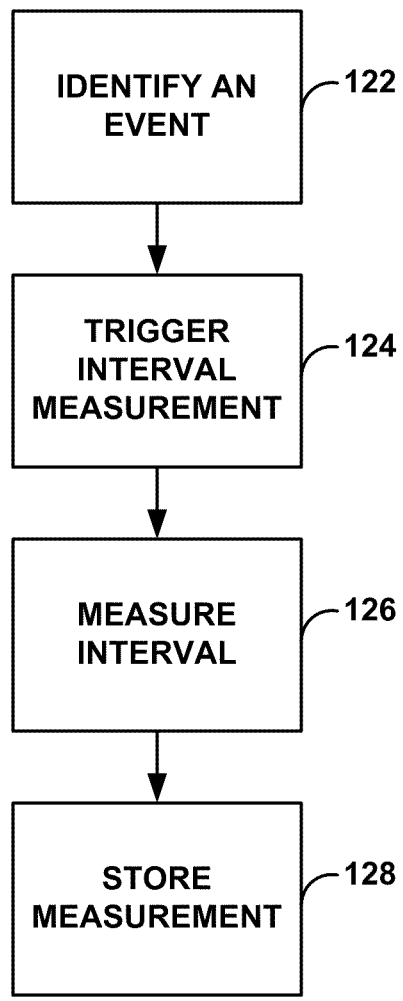
FIG. 9 is a flow diagram illustrating an example operation of an IMD to measure intervals within a cardiac cycle in response to a physiological event.

FIG. 9 is a flow diagram illustrating an example operation of IMD 16 to measure intervals within a cardiac cycle in response to a physiological event. For purposes of illustration, reference is made to IMD 16 and FIGS. 4 and 5. In other examples, some or all of the method of FIG. 9 may be performed by programmer 24 and/or another computing device, such as server 104 (FIG. 7).

At least one of monitors 83 of physiological condition monitor 82, sensor 88, or pressure sensing unit 96 identifies a physiological event (122). For example, heart rate monitor 83A, intrathoracic impedance monitor 83C, or AF/VF/VT monitor 83D may identify a cardiovascular event. Based on the identified physiological event, physiological condition monitor 82, sensor 88, or pressure sensing unit 96 trigger interval measurement unit 84 to measure intervals of segments indicative of cardiac cycles, e.g., QRS width for each cardiac cycle (124). In response, interval measurement unit 84 may measure the QRS widths for one or more cardiac cycles after being triggered (126). In some examples, interval measurement unit 84 may be configured to measure the QRS width for a certain duration after the indication of a physiological event. In some examples, interval measurement unit 84 may wait for a certain duration, and then measure the QRS width.

Interval measurement unit 84 may then store the measured QRS widths, the identified event that triggered the measurement, and when the identified event occurred in memory 90 (128). A clinician or physician may retrieve the information stored in memory 90 to better diagnose patient 14. In particular, the physician or clinician may determine that heart 12 is progressing to a state of heart failure and recommend patient 14 as a candidate for cardiac therapy initiation or modification.

Figure 10:
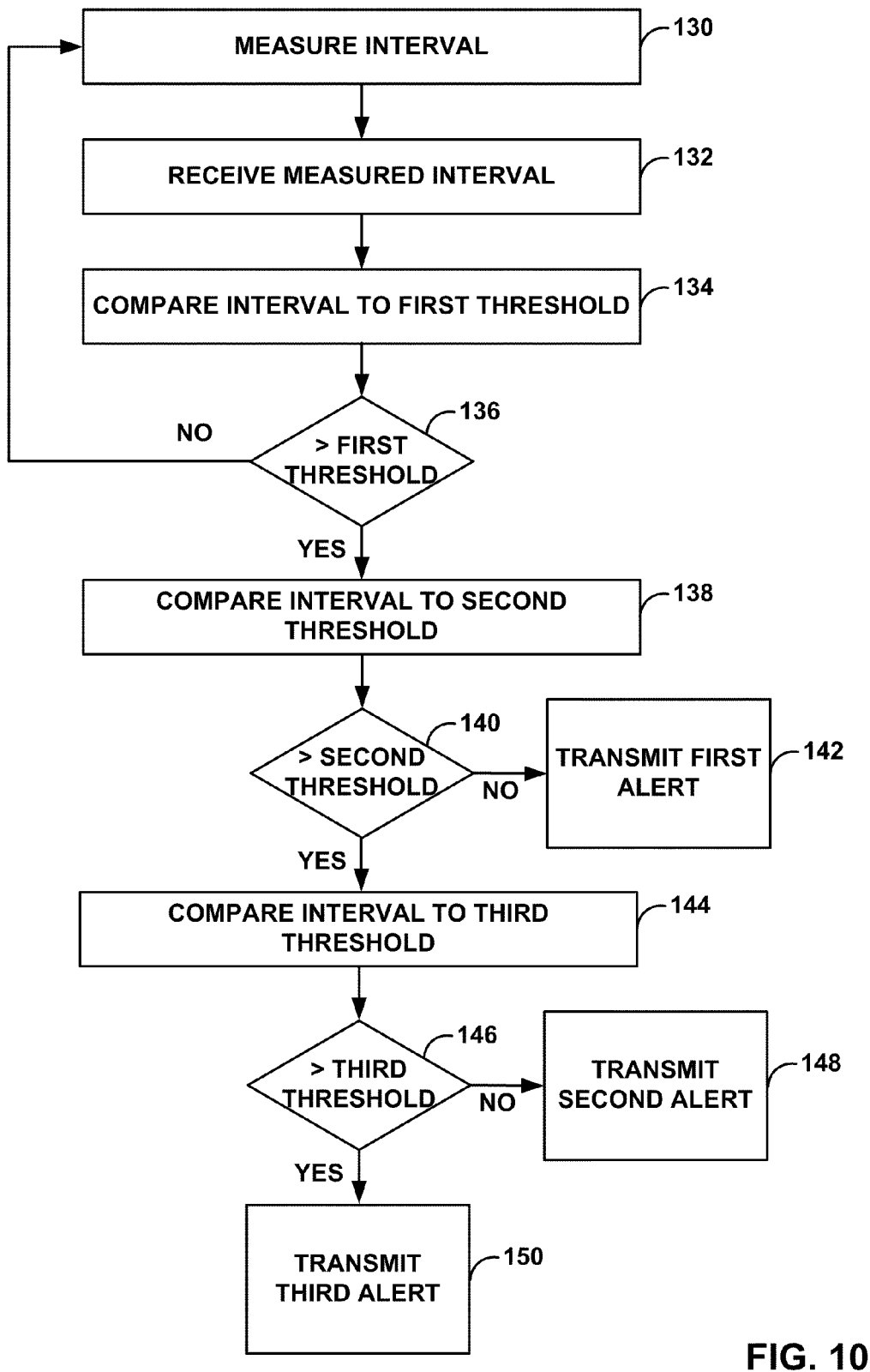
FIG. 10 is a flow diagram illustrating an example method of alerting a patient and/or a physician or clinician based on intervals measured within a cardiac cycle.

FIG. 10 is a flow diagram illustrating an example method of alerting patient 14 and/or a physician or clinician. For purposes of illustration, reference is made to FIG. 5. The flow chart of FIG. 10 begins with the measurement of an interval indicative of a cardiac cycle, e.g., QRS width (130). The measurement of the QRS width may be substantially similar to the measurement of the QRS width described with respect to act 124 of FIG. 8. Processor 86 may receive a measured QRS width value (132).

As described below, acts 134-150 are described as occurring in a sequential fashion. However, aspects of this disclosure should be not considered so limited. In some examples, acts 134-150 may occur in parallel. Processor 86 may compare the measured QRS width to a first threshold QRS width value (134). Processor 86 may then determine whether the measured QRS width is greater than the first threshold (136). If the measured QRS width is less than the first threshold (NO of 134), processor 86 may receive another measured QRS width value (132).

If the measured QRS width is greater than the first threshold (YES of 136), processor 86 may compare the measured QRS width to a second threshold QRS width value (138). Processor 86 may then determine whether the measured QRS width is greater than the second threshold (140). If the measured QRS width is less than the second threshold (NO of 140), processor 86 may transmit a first alert (142). The first alert may be provided only to patient 14 and may recommend that patient 14 visit the clinician or physician.

If the measured QRS width is greater than the second threshold (YES of 140), processor 86 may compare the measured QRS width to a third threshold QRS width value (144). Processor 86 may then determine whether the measured QRS width is greater than the second threshold (146). If the measured QRS width is less than the third threshold (NO of 146), processor 86 may transmit a second alert (148). The second alert may be provided to patient 14 and the physician or clinician and may recommend that patient 14 visit the clinician or physician as soon as possible. If the measured QRS width is greater than the third threshold (YES of 146), processor 86 may transmit a third alert (150). The third alert may be provided to patient 14 and the physician or clinician and may recommend that patient 14 immediately visit an emergency room.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   identifying, with one or more monitors associated with an implantable medical device (IMD) implanted within a patient, at least one physiological event; and
   measuring, with an interval measurement unit, an interval within a cardiac cycle for one or more cardiac cycles in response to the identification of the at least one physiological event to generate one or more measured intervals.

2. The method of claim 1, further comprising:
   storing the one or more of the measured intervals and an indication the of the at least one physiological event.

3. The method of claim 1, wherein the physiological event comprises a cardiovascular event.

4. The method of claim 2, wherein the cardiovascular event comprises at least one of a heart rate, a change in heart rate, an impedance measurement, a heart pressure, bradycardia, tachycardia, and fibrillation.

5. The method of claim 1, wherein the physiological event indicates at least one of a worsening cardiovascular condition, a progression to a state of heart failure, and an improving cardiovascular condition.

6. The method of claim 1, wherein the physiological event comprises at least one of sleep apnea, activity level, and change in activity level.

7. The method of claim 1, further comprising:
   identifying the patient as a candidate for a cardiac therapy based on the measured intervals.

8. The method of claim 1, further comprising:
   transmitting the one or more measured intervals to an external computing device.

9. The method of claim 1, further comprising:
   presenting the one or more measured intervals to a clinician.

10. The method of claim 1, further comprising:
    comparing each one of the measured intervals to a threshold; and
    transmitting an alert to an external computing device based on the comparison.

11. The method of claim 1, wherein the interval comprises a QRS width.

12. An implantable medical device (IMD) comprising:
    one or more monitors configured to identify at least one physiological event of a patient; and
    an interval measurement unit configured to measure an interval within a cardiac cycle for one or more cardiac cycles in response to the identification of the at least one physiological event to generate one or more measured intervals.

13. The IMD of claim 12, wherein the IMD further comprises:
    a memory configured to store the one or more measured intervals and an indication of the at least one physiological event.

14. The IMD of claim 12, wherein the physiological event comprises a cardiovascular event.

15. The IMD of claim 14, wherein the cardiovascular event comprises at least one of a heart rate, a change in heart rate, an impedance measurement, a heart pressure, bradycardia, tachycardia, and fibrillation.

16. The IMD of claim 12, wherein the physiological event indicates at least one of a worsening cardiovascular condition, a progression to a state of heart failure, and an improving cardiovascular condition.

17. The IMD of claim 12, wherein the physiological event comprises at least one of sleep apnea, activity level, and change in activity level.

18. The IMD of claim 12, further comprising:
a telemetry module configured to transmit the one or more measured intervals to an external computing device.

19. The IMD of claim 12, further comprising:
a processor configured to compare each one of the one or more measured intervals to a threshold; and
a telemetry module configured to transmit an alert based on the comparison.

20. The IMD of claim 12, wherein the interval comprises a QRS width.

21. The IMD of claim 12, wherein the one or more monitors comprise at least one of a physiological condition monitor, a sensor, and a pressure sensing module.

22. A system comprising:
one or more monitors associated with an implantable medical device (IMD) configured to:
identify at least one physiological event of a patient;
an interval measurement unit configured to measure an interval within a cardiac cycle for one or more cardiac cycles in response to the identification of the at least one physiological event to generate one or more measured intervals; and
transmit the one or more measured intervals; and
the system further comprising a programmer configured to receive the one or more measured intervals and present the one or more measured intervals.

23. The system of claim 22, further comprising:
a network, wherein the IMD is further configured to transmit the one or more measured intervals via the network to a physician or a clinician.

24. The system of claim 23, where in the physician or clinician identifies the patient as a candidate for cardiac therapy modification based on the one or more measured intervals.

25. The system of claim 23, further comprising:
a network, wherein the IMD is further configured to compare the one or more measured intervals to a threshold and transmit an alert to a physician or a clinician via the network based on the comparison.

26. A non-transitory computer-readable storage medium comprising instructions that cause one or more processors in an implantable medical device (IMD) to:
identify, with one or more monitors, at least one physiological event of a patient; and
measure, with an interval measurement unit, an interval within a cardiac cycle for one or more cardiac cycles in response to the identification of the at least one physiological event to generate one or more measured intervals.

27. A system comprising:
means for identifying at least one physiological event of a patient; and
means for measuring an interval within a cardiac cycle for one or more cardiac cycles in response to the identification of the at least one physiological event to generate one or more measured intervals.

* * * * *